US008663667B2

(12) United States Patent
Bui et al.

(10) Patent No.: US 8,663,667 B2
(45) Date of Patent: Mar. 4, 2014

(54) REFRESHING CREAM FOUNDATION IN GEL FORM

(75) Inventors: Hy Si Bui, Piscataway, NJ (US);
Mohammed Kanji, Edison, NJ (US);
Anita Chon Tong, Garwood, NJ (US);
Chunhua Li, Scotch Plains, NJ (US);
Susan Halpern, Paramus, NJ (US);
Bruno Bavouzet, Gentilly (FR); Yoriko Kawaratani, Carteret, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/379,691

(22) PCT Filed: Jun. 29, 2010

(86) PCT No.: PCT/US2010/040387
§ 371 (c)(1),
(2), (4) Date: Dec. 21, 2011

(87) PCT Pub. No.: WO2011/008540
PCT Pub. Date: Jan. 20, 2011

(65) Prior Publication Data
US 2012/0095113 A1  Apr. 19, 2012

Related U.S. Application Data

(60) Provisional application No. 61/221,292, filed on Jun. 29, 2009, provisional application No. 61/221,295, filed on Jun. 29, 2009, provisional application No. 61/221,377, filed on Jun. 29, 2009, provisional application No. 61/221,278, filed on Jun. 29, 2009, provisional application No. 61/221,289, filed on Jun. 29, 2009, provisional application No. 61/221,262, filed on Jun. 29, 2009, provisional application No. 61/221,388, filed on Jun. 29, 2009, provisional application No. 61/221,400, filed on Jun. 29, 2009, provisional application No. 61/221,255, filed on Jun. 29, 2009, provisional application No. 61/221,285, filed on Jun. 29, 2009, provisional application No. 61/221,326, filed on Jun. 29, 2009, provisional application No. 61/221,291, filed on Jun. 29, 2009, provisional application No. 61/221,265, filed on Jun. 29, 2009.

(51) Int. Cl.
*A61K 8/02* (2006.01)
(52) U.S. Cl.
USPC .................................. 424/401; 424/18.03
(58) Field of Classification Search
USPC .............................. 424/18.03, 401
See application file for complete search history.

(56) References Cited

U.S. PATENT DOCUMENTS

| 2,957,838 A | 10/1960 | Mills, Jr. |
| 3,590,076 A | 6/1971 | Heintzelman et al. |
| 3,699,154 A | 10/1972 | Heintzelman et al. |
| 3,933,511 A | 1/1976 | Heintzelman et al. |
| 3,933,512 A | 1/1976 | Heintzelman et al. |
| 4,041,056 A | 8/1977 | Heintzelman et al. |
| 4,226,889 A | 10/1980 | Yuhas |
| 4,420,588 A | 12/1983 | Yoshioka et al. |
| 4,871,536 A | 10/1989 | Arraudeau et al. |
| 5,032,391 A | 7/1991 | Helioff et al. |
| 5,389,363 A | 2/1995 | Snyder et al. |
| 5,618,524 A | 4/1997 | Bolich et al. |
| 5,620,693 A | 4/1997 | Piot et al. |
| 5,800,816 A | 9/1998 | Brieva et al. |
| 5,911,974 A | 6/1999 | Brieva et al. |
| 5,965,112 A | 10/1999 | Brieva et al. |
| 5,985,298 A | 11/1999 | Brieva et al. |
| 5,998,547 A | 12/1999 | Hohner |
| 6,126,929 A | 10/2000 | Mougin |
| 6,274,152 B1 | 8/2001 | Brieva et al. |
| 6,368,606 B1 | 4/2002 | Dubief et al. |
| 6,464,964 B1 | 10/2002 | Brieva et al. |
| 6,482,400 B1 | 11/2002 | Collin |
| 6,492,455 B1 | 12/2002 | Nadolsky |
| 6,524,564 B1 | 2/2003 | Kim et al. |
| 6,562,322 B2 | 5/2003 | Brieva et al. |
| 6,582,685 B1 * | 6/2003 | Adams et al. .............. 424/70.11 |
| 6,592,854 B1 | 7/2003 | Dupuis |
| 6,716,419 B2 | 4/2004 | Zoltowski et al. |
| 6,780,422 B2 | 8/2004 | Brieva et al. |
| 6,958,148 B1 | 10/2005 | Green et al. |
| 7,005,134 B2 | 2/2006 | Brieva et al. |
| 7,160,550 B2 | 1/2007 | Brieva et al. |
| 7,183,359 B2 * | 2/2007 | Hanna et al. .................. 525/285 |
| 7,186,766 B2 | 3/2007 | Harashina et al. |

(Continued)

FOREIGN PATENT DOCUMENTS

| DE | 100 64 799 A1 | 6/2002 |
| DE | 102004008941 A1 | 9/2005 |

(Continued)

OTHER PUBLICATIONS

U.S. Appl. No. 13/133,176, filed Aug. 2, 2011, Bui et al.
International Search Report Issued Apr. 27, 2011 in PCT/US10/040387 Filed Jun. 29, 2010.
European Office Action Issued Feb. 22, 2013 in Patent Application No. 10 167 788.8.
Hauthal, H. G. Basics, Ingredients, Detergents, Product Safety and Sustainability. Tenside Surf. Det. Jan. 2008, 45 (1), 30-42.
Vertellus, ZeMac(R) E400 Copolymer Technical Data Sheet, May 29, 2008.

(Continued)

*Primary Examiner* — Ali Soroush
(74) *Attorney, Agent, or Firm* — Oblon, Spivak, McClelland, Maier & Neustadt, L.L.P.

(57) ABSTRACT

The present invention is directed to a cosmetic composition includes (a) at least one compound selected from a sugar silicone surfactant, a gelling agent, a polyamine and a hyperbranched polyol; and (b) at least one polar modified polymer.

13 Claims, No Drawings

(56) References Cited

U.S. PATENT DOCUMENTS

| | | |
|---|---|---|
| 7,314,904 B2 | 1/2008 | Nadolsky et al. |
| 7,423,104 B2 | 9/2008 | Lion |
| 7,682,621 B2 | 3/2010 | Lamberty et al. |
| 7,875,265 B2 | 1/2011 | Blin et al. |
| 8,119,110 B2 | 2/2012 | Blin et al. |
| 2002/0136699 A1 | 9/2002 | Dubief et al. |
| 2003/0026816 A1 | 2/2003 | Zoltowski et al. |
| 2003/0082218 A1 | 5/2003 | Ichinohe et al. |
| 2003/0113282 A1 | 6/2003 | Buranachokpaisan |
| 2003/0147931 A1 | 8/2003 | Brieva et al. |
| 2003/0182734 A1 | 10/2003 | Desenne et al. |
| 2004/0170586 A1 | 9/2004 | Ferrari et al. |
| 2004/0186308 A1 | 9/2004 | Koch et al. |
| 2004/0223986 A9 | 11/2004 | Boussouira et al. |
| 2005/0013992 A1 | 1/2005 | Azad et al. |
| 2005/0025736 A1 | 2/2005 | Jachowicz et al. |
| 2005/0180936 A1 | 8/2005 | Pays |
| 2005/0220728 A1 | 10/2005 | Kanji et al. |
| 2006/0013840 A1 | 1/2006 | Lamberty et al. |
| 2006/0084764 A1 | 4/2006 | Hanna et al. |
| 2006/0093568 A1 | 5/2006 | Blin et al. |
| 2006/0104940 A1 | 5/2006 | Heinrichs et al. |
| 2006/0110345 A1 | 5/2006 | Lu et al. |
| 2006/0115444 A1 | 6/2006 | Blin et al. |
| 2006/0147396 A1 | 7/2006 | Monello |
| 2006/0147402 A1 | 7/2006 | Blin et al. |
| 2006/0159642 A1 | 7/2006 | Hanna et al. |
| 2006/0165626 A1 | 7/2006 | Ricard et al. |
| 2006/0188459 A1 | 8/2006 | Heinrichs et al. |
| 2007/0031361 A1* | 2/2007 | Herrmann et al. ......... 424/70.11 |
| 2007/0092468 A1 | 4/2007 | Brieva et al. |
| 2007/0110700 A1 | 5/2007 | Wells et al. |
| 2007/0110702 A1 | 5/2007 | Ehara |
| 2007/0134181 A1 | 6/2007 | Shimizu et al. |
| 2007/0212315 A1 | 9/2007 | Pastor et al. |
| 2007/0256700 A1 | 11/2007 | Bodelin |
| 2007/0258932 A1 | 11/2007 | Bui et al. |
| 2007/0259012 A1 | 11/2007 | Castro et al. |
| 2008/0025934 A1 | 1/2008 | Lebre et al. |
| 2008/0207871 A1 | 8/2008 | Seiler et al. |
| 2009/0060959 A1 | 3/2009 | Igarashi |
| 2009/0130037 A1 | 5/2009 | Thevenet et al. |
| 2010/0310489 A1 | 12/2010 | Barba |
| 2010/0330012 A1 | 12/2010 | Bui et al. |
| 2010/0330015 A1 | 12/2010 | Bui et al. |
| 2010/0330016 A1 | 12/2010 | Bui et al. |
| 2010/0330017 A1 | 12/2010 | Bui et al. |
| 2010/0330022 A1 | 12/2010 | Bui et al. |
| 2010/0330024 A1 | 12/2010 | Bui et al. |
| 2011/0020254 A1 | 1/2011 | Bui et al. |
| 2011/0020255 A1 | 1/2011 | Bui et al. |
| 2011/0020256 A1 | 1/2011 | Bui et al. |
| 2011/0020257 A1 | 1/2011 | Bui et al. |
| 2011/0020260 A1 | 1/2011 | Bui et al. |
| 2011/0020261 A1 | 1/2011 | Bui et al. |
| 2011/0020263 A1 | 1/2011 | Ilekti et al. |
| 2011/0021681 A1 | 1/2011 | Bui et al. |
| 2011/0021683 A1 | 1/2011 | Bui et al. |
| 2011/0038819 A1 | 2/2011 | Bui et al. |
| 2011/0223122 A1 | 9/2011 | Bui et al. |
| 2011/0223123 A1 | 9/2011 | Bui et al. |
| 2011/0280817 A1 | 11/2011 | Ramadan et al. |
| 2011/0280818 A1 | 11/2011 | Kawaratani et al. |
| 2011/0280820 A1 | 11/2011 | Bui et al. |
| 2011/0286950 A1 | 11/2011 | Bui et al. |
| 2011/0286951 A1 | 11/2011 | Bui et al. |
| 2011/0293550 A1 | 12/2011 | Bui et al. |
| 2011/0311467 A1 | 12/2011 | Bui et al. |
| 2012/0004327 A1 | 1/2012 | Bui et al. |
| 2012/0107263 A1 | 5/2012 | Bui et al. |
| 2012/0171137 A1 | 7/2012 | Bradsaw et al. |
| 2012/0171139 A1 | 7/2012 | Bradshaw et al. |

FOREIGN PATENT DOCUMENTS

| | | |
|---|---|---|
| EP | 1 314 415 A1 | 5/2003 |
| EP | 1 854 451 A2 | 11/2007 |
| EP | 2 036 536 A1 | 3/2009 |
| JP | A-07053921 | 2/1995 |
| WO | WO 96/03967 A1 | 2/1996 |
| WO | WO 01/17485 | 3/2001 |
| WO | WO 02/088456 A1 | 11/2002 |
| WO | WO 02 098379 A1 | 12/2002 |
| WO | WO 2006/112690 A1 | 10/2006 |
| WO | WO 2006/127883 A2 | 11/2006 |
| WO | WO 2007/048672 A1 | 5/2007 |
| WO | WO 2007/096400 A1 | 8/2007 |
| WO | WO 2007/139812 A2 | 12/2007 |
| WO | WO 2008/046763 A1 | 4/2008 |
| WO | WO 2009/085888 A1 | 7/2009 |

OTHER PUBLICATIONS

European Search Report dated Mar. 10, 2011, in European Application No. 10167784.7.
European Office Action from European Patent Application No. 10167784.7 dated Mar. 21, 2011 (4 pages).
Perstorp, Boltorn® H2O product data sheet dated Jan. 3, 2008.
Perstorp, Determination of Viscosity for Boltom Dendritic Polymers, Aug. 23, 2011.
Mulkern et al. Polymer, 2000, 41 (9), 3193-3203.
Bergbreiter et al. Tetrahedron Letters, 1997, 38 (21), 3703-3706.
European Search Report issued Apr. 8. 2011, in European Patent Application No. 10167791.2 (with English Abstract).
European Search Report issued Mar. 21, 2011, in European Application No. 10167792.0.
European Search Report issued Apr. 6, 2011, in European Patent Application No. 10167794.6.
European Search Report dated Mar. 14, 2011, issued in European Application No. 10167785.4.
European Patent Office Communication dated Apr. 18, 2011, issued in European Application No. 10167785.4.
European Search Report issued Mar. 10, 2011, in European Application No. 10167790.4.
European Office Action issued in European Patent Application No. 10167790.4 dated Mar. 21, 2011 (4 pages).
International Search Report issued May 20, 2010 in PCT/US09/067332 filed Dec. 9, 2009.
International Search Report issued Aug. 11, 2010 in PCT/US09/68246 filed Dec. 16, 2009.
International Search Report Issued Jul. 26, 2010 in PCT/US09/068151 filed Dec. 16, 2009.
International Search Report issued Jul. 28, 2010 in PCT/US09/68251 filed Dec. 16, 2009.
International Search Report issued Jul. 30, 2010 in PCT/US09/68148 filed Dec. 16, 2009.
http://www.Chemical Book.com/ChemicalProductProperty_EN_CB3748204.htm, Poly (methyl vinyl ether-alt-maleic anhydride), 2010.
International Search Report Issued Jul. 30, 2010 in PCT/US09/068146 filed Dec. 16, 2009.
International Search Report issued Jul. 23, 2010 in PCT/US09/68245 filed Dec. 16, 2009.
Extended European Search Report Issued Nov. 29, 2012 in Patent Application No. 08867867.7.
International Search Report issued May 31, 2010 in PCT/US09/067338 filed Dec. 9, 2009.

* cited by examiner

REFRESHING CREAM FOUNDATION IN GEL FORM

This application is a National Stage of PCT/US10/40387 filed Jun. 29, 2010 and claims the benefit of U.S. provisional applications 61/221,262; 61/221,265; 61/221,278; 61/221,285; 61/221,289; 61/221,292; 61/221,295; 61/221,326; 61/221,377; 61/221,388; 61,221,400; 61/221,255; and 61/221,291 all of which were filed on Jun. 29, 2009.

FIELD OF THE INVENTION

The present invention generally relates to a novel composition which includes: (a) at least one compound selected from a sugar silicone surfactant, a gelling agent, a polyamine and a hyperbranched polyol; and (b) at least one polar modified polymer.

BACKGROUND OF THE INVENTION

Many compositions, especially cosmetic compositions, have been developed for easy and comfortable application onto a targeted substrate. Unfortunately, many of these compositions are in fact difficult to apply and do not possess a smooth feel upon application. Moreover, compositions often have a tendency to feel tacky, yielding poor application and spreadability characteristics. Similarly, the use of silicone resins to impart transfer resistance onto a colored cosmetic product suffers from the same disadvantages disclosed above.

Therefore, it is desirable to provide a composition capable of possessing a good texture and feel with moisturizing and/or long wearing properties without the need for having to use expensive ingredients and/or processing techniques.

BRIEF SUMMARY OF THE INVENTION

A first aspect of the present invention is directed to a composition that includes: (a) at least one compound selected from a sugar silicone surfactant, a gelling agent, a polyamine and a hyperbranched polyol; and (b) at least one polar modified polymer.

The present invention further relates to a composition that includes: (a) at least one compound selected from a sugar silicone surfactant, a gelling agent, a polyamine and a hyperbranched polyol; (b) at least one polar modified polymer; and (c) water.

The present invention further relates to a composition that includes: (a) at least one compound selected from a sugar silicone surfactant, a gelling agent, a polyamine and a hyperbranched polyol; (b) at least one polar modified polymer; and (c) a colorant.

The present invention further relates to a composition that includes: (a) at least one compound selected from a sugar silicone surfactant, a gelling agent, a polyamine and a hyperbranched polyol; (b) at least one polar modified polymer; and (c) at least one oil.

The present invention also relates to compositions which include: (a) a reaction product of at least one polyamine and/or hyperbranched polyol with at least one polar modified polymer; and b) at least one compound selected from a sugar silicone surfactant and a gelling agent.

The present invention also relates to a composition made by combining: (a) at least one compound selected from a sugar silicone surfactant, a gelling agent, a polyamine and a hyperbranched polyol; and (b) at least one polar modified polymer;

A second aspect of the present invention is directed to a method of making up a keratinous substrate comprising applying the above-disclosed composition onto the substrate.

It has been surprisingly discovered that this composition displays a high amount of moisturization to the keratinous substrate and/or is longwearing in the absence of silicone resins and traditional film formers. Further, the composition provides a unique texture and is stable.

DETAILED DESCRIPTION OF THE INVENTION

Other than in the operating examples, or where otherwise indicated, all numbers expressing quantities of ingredients and/or reaction conditions are to be understood as being modified in all instances by the term "about".

"Film former" or "film forming agent" or "film forming resin" as used herein means a polymer which, after dissolution in at least one solvent (such as, for example, water and organic solvents), leaves a film on the substrate to which it is applied, for example, once the at least one solvent evaporates, absorbs and/or dissipates on the substrate.

"Tackiness", as used herein, refers to the adhesion between two substances. For example, the more tackiness there is between two substances, the more adhesion there is between the substances.

"Keratinous substrates", as used herein, include but are not limited to, skin, lips, hair and nails.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

As defined herein, stability is tested by placing the composition in a controlled environment chamber for 8 weeks at 25 C. In this test, the physical condition of the sample is inspected as it is placed in the chamber. The sample is then inspected again at 24 hours, 3 days, 1 week, 2 weeks, weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 37° C., 40° C., 45° C., 50° C., and under freeze-thaw conditions. A composition is considered to lack stability if in any of these tests an abnormality that impedes functioning of the composition is observed. The skilled artisan will readily recognize an abnormality that impedes functioning of a composition based on the intended application.

"Volatile", as used herein, means having a flash point of less than about 100° C. "Non-volatile", as used herein, means having a flash point of greater than about 100° C.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions.

Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

Polar Modified Polymer

According to the present invention, compositions comprising at least one polar modified polymer are provided.

"Polar modified polymer" as used herein refers to "oil-soluble polar modified polymers" and/or "oil-soluble high carbon polar modified polymers."

Oil-Soluble Polar Modified Polymer

According to the present invention, compositions comprising at least one oil-soluble polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil.

Suitable monomers for the hydrophobic homopolymers and/or copolymers include, but are not limited to, cyclic, linear or branched, substituted or unsubstituted, C2-C20 compounds such as, for example, styrene, ethylene, propylene, isopropylene, butylene, isobutylene, pentene, isopentene, isoprene, hexene, isohexene, decene, isodecene, and octadecene, including all ranges and subranges therebetween. Preferably, the monomers are C2-C8 compounds, more preferably C2-C6 compounds, and most preferably C2-C4 compounds such as ethylene, propylene and butylene.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to the present invention, the polar modified polymer is oil-soluble: that is, the polymer does not contain a sufficient amount of hydrophilic unit(s) to render the entire polymer water-soluble or oil-insoluble. According to preferred embodiments, the polar modified polymer contains the same amount of hydrophobic monomer as hydrophilic unit (1:1 ratio) or more hydrophobic monomer than hydrophilic unit. According to particularly preferred embodiments, the polar modified polymer contains 50% or less hydrophilic unit(s) (based on weight of the polymer), 40% or less hydrophilic unit(s), 30% or less hydrophilic unit(s), 20% or less hydrophilic unit(s), 10% or less hydrophilic unit(s), 5% or less hydrophilic unit(s), 4% or less hydrophilic unit(s), or 3% or less hydrophilic unit(s).

Preferably, the polar modified polymer has from about 0.5% to about 10% hydrophilic units, more preferably from about 1% to about 8% hydrophilic units by weight with respect to the weight of the polymer, including all ranges and subranges therebetween. Particularly preferred hydrophilically modified polymers are ethylene and/or propylene homopolymers and copolymers which have been modified with maleic anhydride units.

According to preferred embodiments of the present invention, the polar modified polymer is a wax. According to particularly preferred embodiments, the polar modified wax is made via metallocene catalysis, and includes polar groups or units as well as a hydrophobic backbone. Suitable modified waxes include those disclosed in U.S. patent application publication no. 20070031361, the entire contents of which is hereby incorporated by reference. Particularly preferred polar modified waxes are C2-C3 polar modified waxes.

In accordance with preferred embodiments of the present invention, the polar modified wax is based upon a homopolymer and/or copolymer wax of hydrophobic monomers and has a weight-average molecular weight Mw of less than or equal to 25 000 g/mol, preferably of 1000 to 22 000 g/mol and particularly preferably of 4000 to 20,000 g/mol, a number-average molecular weight Mn of less than or equal to 15 000 g/mol, preferably of 500 to 12 000 g/mol and particularly preferably of 1000 to 5000 g/mol, a molar mass distribution Mw/Mn in the range from 1.5 to 10, preferably from 1.5 to 5, particularly preferably from 1.5 to 3 and especially preferably from 2 to 2.5, which have been obtained by metallocene catalysis. Also, the polar modified wax preferably has a melting point above 75° C., more preferably above 90° C. such as, for example, a melting point between 90° C. and 160° C., preferably between 100° C. and 150° C., including all ranges and subranges therebetween.

In the case of a copolymer wax, it is preferable to have, based on the total weight of the copolymer backbone, 0.1 to 30% by weight of structural units originating from the one monomer and 70.0 to 99.9% by weight of structural units originating from the other monomer. Such homopolymer and copolymer waxes can be made, for example, by the process described in EP 571 882, the entire contents of which is hereby incorporated by reference, using the metallocene catalysts specified therein. Suitable preparation processes include, for example, suspension polymerization, solution polymerization and gas-phase polymerization of olefins in the presence of metallocene catalysts, with polymerization in the monomers also being possible.

Polar modified waxes can be produced in a known manner from the hompopolymers and copolymers described above by oxidation with oxygen-containing gases, for example air, or by graft reaction with polar monomers, for example maleic acid or acrylic acid or derivatives of these acids. The polar modification of metallocene polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable polar modified waxes include, but are not limited to, homopolymers and/or copolymers of ethylene and/or propylene groups which have been modified with hydrophilic units such as, for example, maleic anhydride, acrylate, methacrylate, polyvinylpyrrolidone (PVP), etc. Preferably, the C2-C3 wax has from about 0.5% to about 10% hydrophilic units, more preferably from about 1% to about 8% hydrophilic units by weight with respect to the weight of the wax, including all ranges and subranges therebetween. Particularly preferred hydrophilically modified waxes are ethylene and/or propylene homopolymers and copolymers which have been modified with maleic anhydride units.

Particularly preferred C2-C3 polar modified waxes for use in the present invention are polypropylene and/or polyethylene-maleic anhydride modified waxes ("PEMA," "PPMA," "PEPPMA") commercially available from Clariant under the trade name LICOCARE or LICOCENE, Specific examples of such waxes include products marketed by Clariant under the LicoCare name having designations such as PP207.

Other suitable polar modified polymers include, but are not limited to A-C 573 A (ETHYLENE-MALEIC ANHYDRIDE COPOLYMER; prop Point, Mettler: 106° C.) from Honeywell, A-C 596 A (PROPYLENE-MALEIC ANHYDRIDE COPOLYMER; Drop Point, Mettler: 143° C.) from Honeywell, A-C 597 (PROPYLENE-MALEIC ANHYDRIDE COPOLYMER; Drop Point, Mettler: 141° C.) from Honeywell, ZeMac° copolymers (from VERTELLUS) which are 1:1 copolymers of ethylene and maleic anhydride, polyisobutylene-maleic anhydride sold under the trade name ISOBAM (from Kuraray), polyisoprene-graft-maleic anhydride sold by Sigma Aldrich, poly(maleic anhydride-octadecene) sold by Chevron Philips Chemical Co., poly(ethylene-co-butyl acrylate-co-maleic anhydride) sold under the trade name of Lotader (e.g. 2210, 3210, 4210, and 3410 grades) by Arkema, copolymers in which the butyl acrylate is replaced by other alkyl acrylates (including methyl acrylate [grades 3430, 4404, and 4503] and ethyl acrylate [grades 6200, 8200, 3300, TX 8030, 7500, 5500, 4700, and 4720) also sold by Arkema under the Lotader name, and isobutylene maleic anhydride copolymer sold under the name ACO-5013 by ISP.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orienation (for example, atactic, isotactic or syndiotactic along the backbone).

Preferably, the oil soluble polar modified polymer(s) represent from about 1% to about 30% of the total weight of the composition, more preferably from about 3% to about 17% of the total weight of the composition, and most preferably from about 5% to about 15%, including all ranges and subranges therebetween.

Oil-Soluble High Carbon Polar Modified Polymer

According to the present invention, compositions comprising at least one oil-soluble high carbon polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil. "High carbon" means more than 20 carbon atoms.

Suitable monomers for the hydrophobic homopolymers and/or copolymers include, but are not limited to, cyclic, linear or branched, substituted or unsubstituted, C22-C40 compounds such as, C22-C28 compounds, C24-C26 compounds, C26-C28 compounds, and C30-C38 compounds, including all ranges and subranges therebetween. Preferably, the monomers are C24-26 compounds, C26-C28 compounds or C30-C38 compounds.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to preferred embodiments, the oil-soluble high carbon polar modified polymer is a wax. Also preferably, the oil-soluble high carbon polar modified polymer wax has one or more of the following properties:

a weight-average molecular weight Mw of less than or equal to 30 000 g/mol, preferably of 500 to 10 000 g/mol and particularly preferably of 1000 to 5,000 g/mol, including all ranges and subranges therebetween;

a number-average molecular weight Mn of less than or equal to 15 000 g/mol, preferably of 500 to 12 000 g/mol and particularly preferably of 1000 to 5000 g/mol, including all ranges and subranges therebetween;

a molar mass distribution Mw/Mn in the range from 1.5 to 10, preferably from 1.5 to 5, particularly preferably from 1.5 to 3 and especially preferably from 2 to 2.5, including all ranges and subranges therebetween; and/or a crystallinity of 8% to 60%, preferably 9% to 40%, and more preferably 10% to 30%, including all ranges and subranges therebetween, as determined by differential scanning calorimetry.

According to preferred embodiments relating to a copolymer wax, it is preferable to have, based on the total weight of the copolymer backbone, 0.1 to 30% by weight of structural units originating from the one monomer and 70.0 to 99.9% by weight of structural units originating from the other monomer.

Waxes of the present invention can be based upon homopolymers or copolymers made, for example, by the process described in EP 571 882, the entire contents of which is hereby incorporated by reference. Suitable preparation processes include, for example, suspension polymerization, solution polymerization and gas-phase polymerization of olefins in the presence of catalysts, with polymerization in the monomers also being possible.

Oil-soluble high carbon polar modified polymer wax can be produced in a known manner from the hompopolymers and copolymers described above by oxidation with oxygen-containing gases, for example air, or by graft reaction with polar monomers, for example maleic acid or acrylic acid or derivatives of these acids. The polar modification of polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable oil-soluble high carbon polar modified polymer waxes include, but are not limited to, homopolymers and/or copolymers of C24, C25 and/or C26 groups, copolymers C26, C27 and/or C28 groups, or copolymers of C30-C38 groups, which have been modified with hydrophilic units such as, for example, maleic anhydride, acrylate, methacrylate, polyvinylpyrrolidone (PVP), etc. Preferably, the oil-soluble high carbon polar modified polymer wax has from about 5% to about 30% hydrophilic units, more preferably from about 10% to about 25% hydrophilic units by weight with respect to the weight of the wax, including all ranges and subranges therebetween. Particularly preferred hydrophilically modified waxes are C26, C27 and/or C28 homopolymers and copolymers which have been modified with maleic anhydride units.

Particularly preferred oil-soluble high carbon polar modified polymer waxes for use in the present invention are C26-C28 alpha olefin maleic acid anhydride copolymer waxes commercially available from Clariant under the trade name LICOCARE or LICOCENE. Specific examples of such waxes include products marketed by Clariant under the LicoCare name having designations such as CM 401, which is a maleic anhydride modified wax having a Mw of 2025 and a crystallinity of 11%, C30-C38 olefin/isopropylmaleate/maleic anhydride copolymer sold by Baker Hughes under the name Performa® V 1608, and C24-C26 alpha olefin acrylate copolymer wax commercially available from Clariant under the trade name LICOCARE CA301 LP3346 based on a polar backbone with C24-26 side chains with alternating ester and carboxylic acid groups.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orienation (for example, atactic, isotactic or syndiotactic along the backbone).

Preferably, the oil-soluble high carbon polar modified polymer(s) represent from about 1% to about 30% of the total weight of the composition, more preferably from about 3% to about 17% of the total weight of the composition, and most preferably from about 5% to about 15%, including all ranges and subranges therebetween.

Polyol, Gelling Agent, Sugar Silicone Surfactant, Polyamine

According to the present invention, compositions comprising (1) at least one polar modified polymer and (2) at least one compound selected from a hyperbranched polyol having at least two hydroxyl groups, a sugar silicone surfactant, a polyamine and a gelling agent, are provided. In accordance with the present invention, a composition may contain a polyamine and/or a hyperbranched polyol and/or a sugar silicone surfactant and/or a gelling agent.

Sugar Silicone Surfactant

According to preferred embodiments of the present invention, compositions comprising at least one sugar silicone surfactant are provided. The sugar silicone surfactant of the present invention has the following formula:

$$Sach-X-D_n-X-Sach$$

where Sach represents a saccharide moiety containing multiple hydroxyl groups. Suitable saccharide moieties include, but are not limited to, those based on monosaccharides such as, for example, glucose, fructose, galactose, ribose, mannose, sorbose, etc., and those based one oligosaccharides such as, for example, sucrose, lactose, palatinose, raffinose, lactosucrose, glucosylsucrose, galactosyl-sucrose, xylobiose, etc. Preferably, the saccharide moiety is based on a monosaccharide, most preferably glucose;

X represents a linear or branched, saturated or unsaturated, C1 to C40 hydrocarbon-based group, possibly containing in their chain one or more oxygen, sulphur and/or nitrogen atoms. Preferably, X represents a linear, unsubstituted alkyl group containing at least one N atom, most preferably a linear, unsubstituted alkyl group having 1-6 carbon atoms and at least one N atom;

D represents a silicone based group of the formula $R_2SiO$, where R2 represents a linear or branched, saturated or unsaturated, C1 to C10 hydrocarbon-based group. Preferably, R2 is an unsubstituted C1 to C3 alkyl group (methyl, ethyl, propyl), most preferably a methyl group; and n represents a number between 1 and 1000, preferably between 100 and 500, more preferably between 250 and 400, and more preferably between 300 and 350, including all ranges and subranges therebetween.

Preferably, such sugar silicone surfactants are prepared by reacting a lactone form of the saccharide with an amino form of the D group, thereby forming an alkyl group X having an N atom between the saccharide moiety and the silicone moiety.

Particularly preferred sugar silicone surfactants include gluconamidoethylaminopropylsilicone, lactobionolactonesiloxane, or a mixture thereof.

Preferably, the sugar silicone surfactant represents from about 0.5% to about 25% of the total weight of the composition, more preferably from about 0.75% to about 15% of the total weight of the composition, and most preferably from about 1% to about 10%, including all ranges and subranges therebetween.

Hyperbranched Polyol Compound

According to preferred embodiments of the present invention, compositions comprising at least one hyperbranched polyol compound are provided. In accordance with the present invention, the hyperbranched polyol compound has at least two hydroxyl groups available to react with hydrophilic groups on the backbone of the polar modified wax.

"Hydroxyl number" or "hydroxyl value" which is sometimes also referred to as "acetyl value" is a number which indicates the extent to which a substance may be acetylated; it is the number of milligrams of potassium hydroxide required for neutralization of the acetic acid liberated on saponifying 1 g of acetylated sample. According to preferred embodiments, the at least one hyperbranched polyol has a hydroxyl number between 50 and 250, preferably between 75 and 225, preferably between 100 and 200, preferably between 125 and 175, including all ranges and subranges therebetween such as 90 to 150.

In accordance with the present invention, "hyperbranched polyol" refers to dendrimers, hyperbranched macromolecules and other dendron-based architectures. Hyperbranched polyols can generally be described as three-dimensional highly branched molecules having a tree-like structure. They are characterized by a great number of end groups, at least two of which are hydroxyl groups. The dendritic or "tree-like" structure preferably shows regular symmetric branching from a central multifunctional core molecule leading to a compact globular or quasi-globular structure with a large number of end groups per molecule. Suitable examples of hyperbranched polyols can be found in U.S. Pat. No. 7,423,104, and U.S. patent applications 2008/0207871 and 2008/0286152, the entire contents of all of which are hereby incorporated by reference. Other suitable examples include alcohol functional olefinic polymers such as those available from New Phase Technologies.

Dendrimers tend to be exact, monodisperse structures built layerwise (in generations) around a core moiety, with a polymer branching point in every repeating unit. Hyperbranched polymers tend to possess a number of characteristics which are similar to dendrimers but they tend to be polydispersed and contain relatively linear segments off of which a plurality of highly branched segments are grown or attached.

Furthermore, "hyperbranched polymers" refers to polymers comprising at least two, for example three, polymeric branches, forming either the main branch or a secondary branch, and each comprising at least one at least trifunctional branch point, which may be identical or different, and which is able to form at least two at least trifunctional branch points, different from and independent of one another. Each branch point may be, for example, arranged in the interior of at least one chain. The branches may be, for example, connected to one another by a polyfunctional compound.

As used herein, "trifunctional branch point" means the junction point between three polymer branches, of which at least two branches may be different in chemical constitution and/or structure. For example, certain branches may be hydrophilic, i.e. may predominantly contain hydrophilic monomers, and other branches may be hydrophobic, i.e., may predominantly contain hydrophobic monomers. Further branches may additionally form a random polymer or a block polymer.

As used herein, "at least trifunctional branch" means the junction points between at least three polymeric branches, for example n polymeric branches, of which n–1 branches at least are different in chemical constitution and/or structure.

As used herein, "chain interior" means the atoms situated within the polymeric chain, to the exclusion of the atoms forming the two ends of this chain.

As used herein, "main branch" means the branch or polymeric sequence comprising the greatest percentage by weight of monomer(s).

Branches which are not main branches are called "secondary branches".

According to particularly preferred embodiments of the present invention, the hyperbranched polyol comprises a hydrophobic chain interior. Preferably, the chain interior comprises one or more hydrocarbon groups, one or more silicon-based groups, or mixtures thereof. Particularly preferred chain interiors comprise olefinic polymers or copolymers and/or silicone polymers or copolymers.

Suitable olefinic monomers include, but are not limited to, compounds having from about 2 to about 30 carbon atoms per molecule and having at least one olefinic double bond which are acyclic, cyclic, polycyclic, terminal α, internal, linear, branched, substituted, unsubstituted, functionalized, and/or non-functionalized. For example, suitable monomers include ethylene, propylene, 1-butene, 2-butene, 3-methyl-1-butene, and isobutylene.

Suitable silicone groups for inclusion into the interior chain include "D" groups (for example, dimethicone or substituted dimethicone groups).

An exemplary structure is as follows:

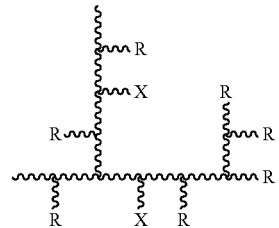

An exemplary structure Where X corresponds to hydroxyl functionality and R corresponds to a methyl group or an alkyl group preferably containing 2-30 atoms.

According to preferred embodiments, the at least one hyperbranched polyol has a molecular weight (Mw) between about 3,000 and 25,000, preferably between 4,000 and 22,000, preferably between 5,000 and 20,000, including all ranges and subranges therebetween such as 4000 to 5500.

According to preferred embodiments, the at least one hyperbranched polyol has a viscosity at 90° F. of between 1,000 and 8,000 centipoise (cps), preferably 2,000 and 7,000 cps, and preferably 3,000 and 6,000 cps, including all ranges and subranges therebetween.

According to preferred embodiments, the at least one hyperbranched polyol is present in the composition of the present invention in an amount ranging from about 0.1 to about 15% by weight, more preferably from about 1 to about 10% by weight, most preferably from about 2 to about 8% by weight, based on the total weight of the composition, including all ranges and subranges within these ranges.

Preferably, the weight ratio of polyol to oil-soluble polar modified polymer is between 4:1 and 1:4, preferably between 3:1 and 1:3, and preferably between 2:1 and 1:2, including all ranges and subranges therebetween.

According to preferred embodiments, the polar modified polymer is in an oil carrier, and the polyol is blended into the oil carrier during production of the compositions of the present invention. Because the polar modified polymer is typically solid at room temperature, the oil carrier is preferably heated to liquefy the polymer prior to combination with the polyol. Preferably, the oil carrier is heated beyond the melting point of the polar modified polymer, typically up to about 70° C., 80° C., 90° C., 100° C. or 110° C. Then, the polar modified polymer is preferably combined with the polyol through blending at room temperature or at a slightly elevated temperature (that is, at a temperature between room temperature and the temperature at which the polar modified polymer was liquefied or melted) such as, for example, about 30° C., 40° C., 50° C., 60° C. or 70° C., for at least about 30 minutes.

According to some embodiments of the present invention, the polyol can be in an aqueous carrier, and the polar modified polymer can be combined with the polyol by combining the oil carrier with the aqueous carrier. According to other embodiments, the polyol does not have to be in an aqueous carrier—the polyol can be added to the oil carrier first, and then water can be subsequently added to the mixture.

Polyamine Compound

According to preferred embodiments of the present invention, compositions comprising at least one polyamine compound are provided. In accordance with the present invention, the polyamine compound has at least two primary amine groups available to react with hydrophilic groups of the polar modified polymer.

According to particularly preferred embodiments, the polyamine compound is a polyalkyleneimine, preferably a C2-C5 polyalkyleneamine compound, more preferably a polyethyleneimine or polypropyleneimine. Most preferably, the polyalkylenamine is polyethyleneimine ("PEI"). The polyalkyleneamine compound preferably has an average molecular weight range of from 500-200,000, including all ranges and subranges therebetween.

According to preferred embodiments, compositions of the present invention contain polyethyleneimine compounds in the form of branched polymers. Commercially available examples of such polymers are available from BASF under the tradename LUPASOL or POLYIMIN. Non-limiting examples of such polyethyleneimines include Lupasol® PS, Lupasol® PL, Lupasol® PR8515, Lupasol® G20, Lupasol® G35.

According to other embodiments of the present invention, polyamines such as polyethyleneimines and polypropyleneimines can be in the form of dendrimers. Non-limiting examples of such dendrimers are manufactured by the company DSM, and/or are disclosed in U.S. Pat. No. 5,530,092 and U.S. Pat. No. 5,610,268, the contents of which are hereby incorporated by reference. Commercially available examples of such polymers include polyamidoamine or polypropyleneimine polymers from DENDRITECH sold under the STARBURST® name.

According to other embodiments of the present invention, derivatives of polyalkyleneamines are suitable polyamines. Such derivatives include, but are not limited to, alkylated derivatives, the addition products of alkylcarboxylic acids to polyalkyleneamines, the addition products of ketones and of aldehydes to polyalkyleneamines, the addition products of isocyanates and of isothiocyanates to polyalkyleneamines, the addition products of alkylene oxide or of polyalkylene oxide block polymers to polyalkyleneamines, quaternized derivatives of polyalkyleneamines, the addition products of a silicone to polyalkyleneamines, and copolymers of dicarboxylic acid and polyalkyleneamines. Even further suitable polymamines include, but are not limited to, polyvinyl imidazoles (homopolymers or copolymers), polyvinylpyridines (homopolymers or copolymers), compounds comprising vinylimidazole monomers (see, for example, U.S. Pat. No. 5,677,384, hereby incorporated by reference), and polymers based on amino acids containing a basic side chain (preferably selected from proteins and peptides comprising at least 5%, preferably at least 10% of amino acids selected from histidine, lysine and arginine). Such suitable polyamines as described above include those disclosed and described in U.S. Pat. No. 6,162,448, the contents of which are hereby incorporated by reference. Commercially available examples of such polymers include polyvinylamine/formamide such as those sold under the Lupamine® name by BASF, chitosan from vegetable origin such as those sold under the Kiosmetine® or Kitozyme® names, or copolymer 845 sold by ISP.

According to preferred embodiments, the at least one polyamine compound is present in the composition of the present invention in an amount ranging from about 0.05 to about 20% by weight, more preferably from about 0.2 to about 10% by weight, more preferably from about 0.5 to about 5% by weight, based on the total weight of the composition, including all ranges and subranges within these ranges.

Preferably, the amount of polyamine compound reacted with the polar modified polymer is such that at least two amine groups on the polyamine compound react with the polar modified polymer to form links or bonds between the amine groups and the hydrophilic groups of the polar modified polymer. The appropriate amount of polyamine compound to react with the polar modified polymer to obtain a reaction product can be easily determined, taking into account the number/amount of reactive amine groups on the polyamine compound and the number/amount of corresponding reactive groups on the polar modified polymer (for example, maleic anhydride groups). According to preferred embodiments, excess polar modified polymer (as determined by the relative number/amount of corresponding reactive groups on the polymer as compared to the reactive amine groups on the polyamine) is reacted with polyamine. Preferably, the polyamine to polar modified ratio is between 0.005 and 1, preferably between 0.006 and 0.5, and preferably between 0.007 and 0.1, including all ranges and subranges therebetween.

Gelling Agent

According to preferred embodiments of the present invention, compositions comprising at least one gelling agent chosen from cellulose, and derivates thereof are provided. Such gelling agents are typically found in the aqueous phase of a composition.

Examples of suitable cellulose, and derivatives thereof include, but are not limited to:

cellulose polymers such as hydroxyethylcellulose, hydroxypropylcellulose, methylcellulose, ethylhydroxyethylcellulose, carboxymethylcellulose, and quaternized cellulose derivatives;

cellulosic thickeners, for example, hydroxyethylcellulose, hydroxypropylcellulose, and carboxymethylcellulose, guar gum and its derivatives, such as hydroxypropylguar, gums of microbial origin, such as xanthan gum and scleroglucan gum;

quaternized cellulose derivatives and polyacrylates containing non-cyclic amine side groups. The quaternized cellulose derivatives may include, for example:

quaternized celluloses modified with groups comprising at least one fatty chain, such as alkyl, arylalkyl, and alkylaryl groups comprising at least 8 carbon atoms, and mixtures thereof;

quaternized hydroxyethylcelluloses modified with groups comprising at least one fatty chain, such as alkyl, arylalkyl, and alkylaryl groups comprising at least 8 carbon atoms, and mixtures thereof;

polyquaternium-37 (commercially available from Cognis under the trademark name Ultragel 300 and from Ciba under the trademark name SalCARE); hydroxyalkyl cellulose polymers and alkyl hydroxyalkyl cellulose polymers such as hydroxyethyl cellulose (commercially available from Amerchol and The Dow Chemical Company and Hercules under the tradenames Cellosize and Natrosol), hydroxypropyl cellulose (commercially available from Hercules under the tradename Klucel) and cetyl hydroxyethyl cellulose (commercially available from Hercules under the tradename Natrosol);

carboxymethyl cellulose (commercially available from Hercules under the tradename Aqualon), natural or synthetic gums, and starches;

quaternized alkylhydroxyethylcelluloses containing C8-C30 fatty chains include, for instance, the products Quatrisoft LM 200, Quatrisoft LM-X 529-18-A, Quatrisoft LM-X 529-18B (C12 alkyl), and Quatrisoft LM-X 529-8 (C18 alkyl) sold by the company Amerchol, and the products Crodacel QM, Crodacel QL (C12 alkyl) and Crodacel QS (C18 alkyl) sold by the company Croda.

Particularly preferred thickening agents are polysaccharides or polysaccharide derivatives such as hydroxyethyl cellulose, hydroxypropyl cellulose, methyl cellulose, xanthan gum, guar gum, hydroxymethylcellulose derivatives such as hydroxypropyl methylcellulose and hydroxybutyl methyl cellulose, starch and starch derivatives.

Particularly preferred rheology-modifying agents are cetyl hydroxyethyl cellulose, quaternized celluloses and hydroxyethylcelluloses.

Preferably, the gelling agent is present in the composition of the present invention in an amount ranging from about 0.1% to about 10.0% by weight, preferably from about 0.5% to about 5.0% by weight, preferably from about 1.0% to about 4.0% by weight of the total weight of the composition, including all ranges and subranges therebetween.

Reaction Product

According to preferred embodiments of the present invention, the polar modified polymer is reacted with the polyamine compound, in the presence of water in, at minimum, an amount sufficient to solubilize the polyamine, to form a reaction product. In accordance with the preferred embodiments, the reaction product is water-insoluble.

Although not wanting to be bound by any particular theory, it is believed that at a temperature below 100° C., the reaction of the polar modified polymer with the primary amine group of the polyamine opens the anhydride ring to form a half acid and half amide crosslinked product. However, at a temperature above 100° C., the reaction of the polar modified polymer with the primary amine group of the polyamine opens the anhydride ring to form an imide crosslinked product. The former product is preferred over the latter product. It is not necessary for all amine groups and all hydrophilic groups to react with each other to form the reaction product. Rather, it is possible that the composition may contain free polyamine and/or free polar modified polymer in addition to the reaction product.

Although not wanting to be bound by any particular theory, it is also believed that the polyamine(s) can be non-covalently assembled with the polar modified polymer(s) by electrostatic interaction between an amine group of the polyamine and a hydrophilic group (for example, carboxylic acid group associated with maleic anhydride groups) of the polar modified polymer to form a supramolecule. For example, with specific reference to maleic anhydride groups, in the presence of water these groups can open to form dicarboxylic acid groups which can interact with protonated primary amines of the polyamine through ionic interaction to form a polymer-polymer complex with hydrophilic core crosslinkers and a hydrophobic network that act as supramolecular capsule. If a large amount of maleic anhydride groups are present, the secondary amine groups of polyamine are also protonated and interact with alkyl carboxylates.

According to preferred embodiments, the polar modified polymer is in an oil carrier, and the polyamine compound is in an aqueous carrier, and the reaction occurs by combining the oil carrier and the aqueous carrier. Because the polar modified polymer is typically solid at room temperature, the oil carrier is preferably heated to liquefy the polymer prior to combination with the aqueous carrier. Preferably, the oil carrier is heated beyond the melting point of the polar modified polymer, typically up to about 80° C., 90° C. or 100° C.

Without intending to be bound by any particular theory, it is believed that the reason for this is that due to the chemical and physical reactions which take place when the polar modified polymer is combined with the polyamine, the subsequent reaction product that is formed is surprisingly and unexpectedly able to entrap large amounts of water molecules within its hydrophobic matrix. The resultant product is eminently capable of forming a film, is self-emulsifying, waterproof. Moreover, the product is both stable and capable of carrying various types of ingredients.

Similarly, according to preferred embodiments of the present invention, the reaction of the polar modified polymer and polyol in an anhydrous system (oil phase only) can create a reaction product. Without intending to be bound by any particular theory, it is believe that the reaction product of the polar modified polymer and the hyperbranched polyol is an elastomer-type compound having ester linkages which can swell in polar solvents or can disperse into the water phase.

Water

According to preferred embodiments, the composition of the present invention further contains water. The water is typically present in an amount of from about 5% to about 50% by weight, such as from about 10% to about 40% by weight, such as from about 25% to about 35% by weight, including all ranges and subranges therebetween, all weights being based on the total weight of the composition. According to particularly preferred embodiments, sufficient water is present to form a water-in-oil emulsion.

Optional Ingredients

Gelling Agent

It may be desirable to employ an additional gelling agent, other than cellulose and derivatives thereof. Examples of such other gelling agents include:

water-soluble gelling polymers such as:

proteins, such as proteins of plant origin, for instance wheat proteins and soy proteins; proteins of animal origin such as keratins, for example keratin hydrolysates and sulphonic keratins;

anionic, cationic, amphoteric or nonionic chitin or chitosan polymers; and synthetic thickeners such as crosslinked homopolymers of acrylic acid and of acrylamidopropanesulphonic acid;

fatty acid amides such as coconut diethanolamide and monoethanolamide, and oxyethylenated monoethanolamide of carboxylic acid alkyl ether, and associative polymers.

Cationic associative polymers may include, but are not limited to:

cationic associative polyurethanes which may be formed from diisocyanates and from various compounds with functions containing a labile hydrogen. The functions containing a labile hydrogen may be chosen from alcohol, primary and secondary amine, and thiol functions, giving, after reaction with the diisocyanate functions, polyurethanes, polyureas, and polythioureas, respectively. The expression "polyurethanes which can be used according to the present invention" encompasses these three types of polymer, namely polyurethanes per se, polyureas and polythioureas, and also copolymers thereof. Example of such compounds include, but are not limited to, methylenediphenyl diisocyanate, methylenecyclohexane diisocyanate, isophorone diisocyanate, tolylene diisocyanate, naphthalene diisocyanate, butane diisocyanate, and hexane diisocyanate; and carboxyvinyl polymers, acrylic acid/polyallyl sucrose copolymers, polyacrylic compounds and acrylic acid/ethyl acrylate copolymers (commercially available under the CARBOPOL tradenames).

If present, such other gelling agent is preferably present in the composition of the present invention in an amount ranging from about 0.1% to about 10.0% by weight, preferably from about 0.5% to about 5.0% by weight, preferably from about 1.0% to about 4.0% by weight of the total weight of the composition.

Volatile Solvent Other than Water

The cosmetic composition of the present invention can comprise at least one volatile solvent. In an embodiment of the present invention, the at least one volatile solvent may be chosen from a volatile silicone oil or a volatile non-silicone oil.

Suitable volatile silicone oils include, but are not limited to, linear or cyclic silicone oils having a viscosity at room temperature less than or equal to 6 cSt and having from to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (3 St) from Dow Corning | 102 | 3 |

Suitable volatile non-silicone oils may be selected from volatile hydrocarbon oils, alcohols, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate and their mixtures. Preferably, the volatile non-silicone oils have a flash point of at least 40° C.

Non-limiting examples of volatile non-silicone oils are listed in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin C11-C13) | 62 |
| Isopar H (isoparaffin C11-C12) | 56 |

If present, the at least one volatile solvent is present in the composition in an amount of from about 20 to about 90% by weight, such as from about 30 to about 80% by weight, and from about 35 to about 75% by weight, all weights based on the total weight of the composition, including all ranges and subranges therebetween.

Non-volatile Solvent for Oil-soluble Polar Modified Polymer

The cosmetic composition of the present invention can comprise at least one non-volatile oil capable of dissolving the oil-soluble polar modified polymer. As used herein, the term "non-volatile" means having a boiling point of greater than about 100 degrees C.

Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol; and mixtures thereof.

Further, examples of hydrocarbon oils which may be used include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

If present, the at least one non-volatile solvent is preferably present in the composition of the invention in an amount of from about 1% to about 20% by weight, such as from about 1.5% to about 10% by weight, such as from about 2% to about 5% by weight, all weights based on the total weight of the composition.

The composition of the present invention may also include other ingredients. Examples thereof include, but are not limited to, colorants such as dyes and pigments, co-solvents (volatile and/or non-volatile), waxes, plasticizers, preservatives, fillers, active ingredients such as those used to treat skin and hair and sunscreens.

It has surprisingly been discovered that the composition of the present invention is highly transfer resistant and long wearing, and in order to be effective as a base/matrix for carrying insoluble ingredients, does not require the use of silicone resins, emulsifiers or gelling agents. The resulting product is also able to provide a composition capable of possessing a gel texture and nice feel with highly moisturizing and long wearing properties without the need for having to use expensive ingredients and/or processing techniques The composition of the present invention may be used for any application in which it is desirable to employ a waterproof film, capable of carrying insoluble ingredients such as, for example, pigments, and which is stable, easily spreadable, and comfortable to apply.

The present invention is further described in terms of the following non-limiting examples. Unless otherwise indicated, all parts and percentages are on a weight-by-weight percentage basis.

EXAMPLE 1

A cosmetic composition was prepared containing the below-disclosed ingredients.

| | |
|---|---|
| isododecane | 30.00 |
| isohexadecane | 2.25 |
| PP207* | 6.75 |
| polyglyceryl-2 triisostearate | 2.35 |
| DI Water | 23.00 |
| Cellulose | 0.15 |
| Lupasol G 35 PEI (PolyEthyleneImine) 50% solid/50% water | 4.00 |
| hyperbranched polyol | 5.00 |
| sugar silicone surfactant (40% water) | 15.00 |
| TITANIUM DIOXIDE | 7.82 |
| IRON OXIDES | 1.46 |
| IRON OXIDES | 0.52 |
| IRON OXIDES | 0.20 |
| DISODIUM EDTA | 0.20 |
| propylene glycol | 0.50 |
| PHENOXY-2 ETHANOL | 0.40 |
| CHLORPHENESIN | 0.20 |
| ETHYL PARABEN | 0.20 |
| | 100.00 |

*PP207 is a linear polypropylene-ethylene-maleic anhydride copolymer wax commercially available from Clariant under the tradename LICOCARE PP207 LP 3349.

Procedure
1. In container A, PP207 was melted in the isohexadecane and isododecane until fully dissolved. The temperature was brought to 90° C.
2. While maintaining the temperature, the hyperbranched polyol, emulsifier and pigment grind were added to container A until fully dissolved.
3. In separate container B, sugar silicone surfactant, water, Polyethyleneimine, cellulose, and preservatives were mixed at 90 C
4. B was added to A slowly at high sheer (~700 rpm).
5. Heat was maintained at 70° C.-80° C. for 20 minutes while maintaining high sheer mixing.
6. The mixture was cooled to room temperature while mixing.

EXAMPLE 2

A cosmetic composition was prepared containing the below-disclosed ingredients.

| | |
|---|---|
| isohexadecane | 2.25 |
| isododecane | 40.15 |
| PP207* | 6.75 |
| polyglyceryl-2 triisostearate | 2.50 |
| DI Water | 25.50 |
| Cellulose | 0.20 |
| Sugar Silicone | 10.00 |
| Polyethyleneimine | 0.75 |
| TITANIUM DIOXIDE | 7.82 |
| IRON OXIDES | 1.46 |
| IRON OXIDES | 0.52 |
| IRON OXIDES | 0.20 |
| DISODIUM EDTA | 0.20 |
| propylene glycol | 0.50 |
| PHENOXY-2 ETHANOL | 0.80 |
| CHLORPHENESIN | 0.20 |
| ETHYL PARABEN | 0.20 |
| TOTAL | 100.00 |

*PP207 is a linear polypropylene-ethylene-maleic anhydride copolymer wax commercially available from Clariant under the tradename LICOCARE PP207 LP 3349.

Procedure:
1. In container A, PP207 was melted in the isohexadecane and isododecane until fully dissolved. The temperature was brought to 90° C.
2. While maintaining the temperature, the emulsifier and pigment grind were added to container A until fully dissolved.
3. In separate container B, sugar silicone surfactant, water, Polyethyleneimine, cellulose, and preservatives were mixed at 90 C.
4. B was added to A slowly at high sheer (~700 rpm).
5. Heat was maintained at 70° C.-80° C. for 20 minutes while maintaining high sheer mixing.
6. The mixture was cooled to room temperature while mixing.

EXAMPLE 3

Lip Composition

| Phase | Chemical Name | Example 3 |
|---|---|---|
| A | Non-volatile Solvent | Q.S. |
| A | Polyethylene 400 | 8.00 |
| A | Linear polypropylene-ethylene-maleic anhydride copolymer wax | 9.33 |
| A | Pigment | 3.50 |
| A | Mica | 2.00 |
| B | Deionized Water | 22.50 |
| B | PEI-35 | 0.25 |

-continued

| Phase | Chemical Name | Example 3 |
|---|---|---|
| B | Glycerin | 3.00 |
| B | Sugar Silicone Surfactant | 10.00 |
| | Total | 100.00 |

Procedure:
1. The following were added to a suitable size beaker A and heated to 95 Celsius degrees: non-volatile solvent, polyethylene 400, and linear polypropylene-ethylene-maleic anhydride copolymer wax.
2. When enough solids had melted, the contents were mixed with moderate speed until all solids had melted at 95 Celsius degrees.
3. The temperature was slightly lowered to 85 Celsius degrees and pigments and mica were added.
4. The contents of main beaker A was transferred to a Silverson mixer for emulsification while maintaining the temperature at 85-90 Celsius degrees.
5. In a separate beaker 2, glycerin, sugar silicone surfactant and PEI-35 were added into DI water, mixed and heated to 85 Celsius degrees.
6. The contents of side beaker B was added dropwise into the beaker A while emulsifying at 9000 rpm under the Silverson mixer for 30 minutes. Afterward, the emulsification speed was lowered to 2000 rpm for 5 minutes.
7. The contents were poured into lipstick molds at 80 Celsius degrees.
8. The lipstick in molds was placed in a cooling tunnel for 15 minutes at −10 Celsius degrees. Once cooled, the lipstick in molds were removed from the cooling tunnel to equilibrate to 25 Celsius degrees and removed from mold after lipsticks had thawed to 25 Celsius degrees.

EXAMPLE 4

Lip Composition

| Phase | Chemical Name | Example 4 |
|---|---|---|
| A | Non-volatile Solvent | Q.S. |
| A | Linear polypropylene-ethylene-maleic anhydride copolymer wax | 10.00 |
| A | Pigment | 3.50 |
| A | Mica | 2.00 |
| B | Deionized Water | 40.00 |
| B | PEI-35 | 0.25 |
| B | Glycerin | 3.00 |
| B | Sugar Silicone Surfactant | 10.00 |
| | Total | 100.00 |

Procedure:
1. The following were added to a suitable size beaker A and heated to 95 Celsius degrees: non-volatile solvent and linear polypropylene-ethylene-maleic anhydride copolymer wax.
2. When enough solids had melted, the contents were mixed with moderate speed until all solids had melted at 95 Celsius degrees.
3. The temperature was slightly lowered to 85 Celsius degrees and pigments and mica were added.
4. The contents of main beaker A was transferred to a Silverson mixer for emulsification while maintaining the temperature at 85-90 Celsius degrees.
5. In a separate beaker 2, glycerin, sugar silicone surfactant and PEI-35 were added into DI water and mixed and heated to 85 Celsius degrees.
6. The contents of side beaker B was added dropwise into the beaker A while emulsifying at 9000 rpm under the Silverson mixer for 30 minutes. Afterward, the emulsification speed was lowered to 2000 rpm for 5 minutes until contents were cooled to 25 Celsius degrees.
7. The contents of main beaker A were poured into the container.

EXAMPLE 5

| Phase | Chemical Name | Example 5 |
|---|---|---|
| A | Non-volatile Solvent | Q.S. |
| A | Polyethylene 400 | 8.00 |
| A | $C_{26-28}$ a-olefin-maleic acid anhydride copolymer wax | 7.00 |
| A | Pigment | 3.50 |
| A | Mica | 2.00 |
| B | Deionized Water | 22.50 |
| B | PEI-35 | 0.25 |
| B | Glycerin | 3.00 |
| B | Sugar Silicone Surfactant | 10.00 |
| | Total | 100.00 |

Procedure:
1. The following were added to a suitable size beaker A and heated to 95 Celsius degrees: non-volatile solvent, polyethylene 400, and Oil-soluble high carbon polar modified polymer.
2. When enough solids had melted, the contents were mixed with moderate speed until all solids had melted at 95 Celsius degrees.
3. The temperature was slightly lowered to 85 Celsius degrees and pigments and mica were added.
4. The contents of main beaker A were transferred to a Silverson mixer for emulsification while maintaining the temperature at 85-90 Celsius degrees.
5. In a separate beaker 2, glycerin, sugar silicone surfactant and PEI-35 were added into DI water, mixed and heated to 85 Celsius degrees.
6. The contents of side beaker B were added dropwise into the beaker A while emulsifying at 9000 rpm under the Silverson mixer for 30 minutes. Afterward, the emulsification speed was lowered to 2000 rpm for 5 minutes.
7. The contents were poured into lipstick molds at 80 Celsius degrees.
8. The lipstick in molds was placed in a cooling tunnel for 15 minutes at −10 Celsius degrees. Once cooled, the lipstick in molds were removed from the cooling tunnel to equilibrate to 25 Celsius degrees and removed from the molds after lipsticks had thawed to 25 Celsius degrees.

EXAMPLE 6

| Phase | Chemical Name | Example 6 |
|---|---|---|
| A | Non-volatile Solvent | Q.S. |
| A | $C_{26-28}$ a-olefin-maleic acid anhydride copolymer wax | 7.00 |
| A | Pigment | 3.50 |
| A | Mica | 2.00 |
| B | Deionized Water | 40.00 |
| B | PEI-35 | 0.25 |
| B | Glycerin | 3.00 |
| B | Sugar Silicone Surfactant | 10.00 |
| | Total | 100.00 |

Procedure:
1. The following were added to a suitable size beaker A and heated to 95 Celsius degrees: non-volatile solvent and Oil-soluble high carbon polar modified polymer.
When enough solids had melted, the contents were mixed with moderate speed until all solids had melted at 95 Celsius degrees.
The temperature was slightly lowered to 85 Celsius degrees and pigments and mica were added.
2. The contents of main beaker A were transferred to a Silverson mixer for emulsification while maintaining the temperature at 85-90 Celsius degrees. In a separate beaker 2, glycerin, sugar silicone surfactant and PEI-35 were added into DI water and mixed and heated to 85 Celsius degrees.
3. The contents of side beaker B were added dropwise into the beaker A while emulsifying at 9000 rpm under the Silverson mixer for 30 minutes. Afterward, the emulsification speed was lowered to 2000 rpm for 5 minutes until the contents were cooled to 25 Celsius degrees.
4. The contents of main beaker A was poured into container.

EXAMPLE 7

| Phase | Component | Example 7 |
|---|---|---|
| A | C20-C40 Pareth-10 | 7.00 |
| A | Propylene-ethylene-Maleic Anhydride Copolymer | 7.00 |
| A | Isohexadecane | 2.33 |
| A | Iron Oxides | 8.0 |
| A | Isododecane | 30.92 |
| A | Propylparaben | 0.2 |
| B | DI Water | 19.00 |
| B | Disodium EDTA | 0.1 |
| B | Potassium Cetyl Phosphate | 2.00 |
| B | Methylparaben | 0.25 |
| B | Gluconamidoethylaminopropylsilocone (and) Alcohol | 20.00 |
| B | Polyethyleneimine (PEI-35) | 2.00 |
| C | Simethicone | 0.1 |
| D | Phenoxyethanol (and) Methylparaben (and) Isopropylparaben (and) Isobutylparaben (and) Butylparaben | 1.1 |
| | Total | 100 |

Procedure:
1. In the main beaker A, the following were added: Isododecane, C20-C40 Pareth-10, Polypropylene-ethylene-Maleic Anhydride Copolymer wax, and propylparaben. The contents were then heated to 90° C. until all solids melted.
2. Added Iron Oxides into main beaker and started homogenizing batch for 1 h at 850 RPM. (Temperature maintained at 85-90° C.)
3. In another beaker B, added deionized water, Disodium EDTA, Potassium Cetyl Phosphate, Methylparaben, Gluconamidoethylaminopropylsilocone (and) Alcohol and Polyethyleneimine (PEI-35). Mixed until uniform. Heated contents to 90° C.
4. Slowly added contents of beaker B to beaker A. Then added Simethicone to the mixture. The gel formation was observed in 5 minutes after mixing A and B.
5. During the gel formation, slowed down the mixing speed from 250 RPM to 100 RPM to 50 RPM.
6. Once the gel network became thick enough, changed to sweep blade. Started cooling using 50 RPM.
7. At 35° C., added a mixture of Phenoxyethanol (and) Methylparaben (and) Isopropylparaben (and) Isobutylparaben (and) Butylparaben.
8. Continued cooling to 25° C.

EXAMPLE 8

Lip Stick Composition

| Phase | Chemical Name | Ex 8 |
|---|---|---|
| A | Polyglyceryl-2 Triisosterate | 3.00 |
| A | Octyldodecyl Neopantanoate | 15.23 |
| A | Hydrogenated Polydecene | 15.23 |
| A | Hyperbranched polyol | 5.00 |
| A | Polyethylene 400 | 8.00 |
| A | Polypropylene-ethylene-maleic anhydride copolymer wax | 7.00 |
| A | Color Pigments | 5.00 |
| A | Tricaprylin | 13.80 |
| A | Mica | 2.00 |
| B | Deionized Water | 22.50 |
| B | Glycerin | 3.00 |
| B | PEI-35 | 0.25 |

Procedure:
1. The following were added to a suitable size beaker A and heated to 95 Celsius degrees: Polyglyceryl-2 Triisosterate, octyldodecyl neopantanoate, hydrogenated polydecene, Hyperbranched polyol, polyethylene 400, Polypropylene-ethylene-maleic anhydride copolymer wax.
2. When enough solids had melted, the contents were mixed with moderate speed until all solids had melted at 95 Celsius degrees.
3. The temperature was slightly lowered to 85 Celsius degrees and pigments, tricaprylin and mica were added.
4. The contents of main beaker A was transferred to a Silverson mixer for emulsification while maintaining the temperature at 85-90 Celsius degrees.
5. In a separate beaker 2, glycerin and PEI-35 were added into DI water and mixed and heated to 85 Celsius degrees.
6. The contents of side beaker B was added dropwise into the beaker A while emulsifying at 9000 rpm under the Silverson mixer for 30 minutes.
7. Afterward, the emulsification speed was lowered to 2000 rpm for 5 minutes.

8. The contents were poured into lipstick molds at 80 Celsius degrees.
9. The lipstick in molds was placed in a cooling tunnel for minutes at −10 Celsius degrees. Once cooled, the lipstick in molds were removed from the cooling tunnel to equilibrate to 25 Celsius degrees and removed from mold after lipsticks had thawed to 25 Celsius degrees.

EXAMPLE 9

Lip Gloss Composition

| Phase | Chemical Name | Ex 9 |
| --- | --- | --- |
| A | Polyglyceryl-2 Triisosterate | 6.00 |
| A | Octyldodecyl Neopantanoate | 8.95 |
| A | Hydrogenated Polydecene | 8.95 |
| A | Hyperbranched polyol | 5.00 |
| A | Polypropylene-ethylene-maleic anhydride copolymer wax | 7.00 |
| A | Color Pigments | 5.00 |
| A | Tricaprylin | 13.80 |
| A | Mica | 2.00 |
| B | Deionized Water | 40.00 |
| B | Glycerin | 3.00 |
| B | PEI-35 | 0.25 |

1. The following were added to a suitable size beaker A and heated to 95 Celsius degrees: Polyglyceryl-2 Triisosterate, octyldodecyl neopantanoate, hydrogenated polydecene, Hyperbranched polyol, Polypropylene-ethylene-maleic anhydride copolymer wax.
2. When enough solids had melted, the contents were mixed with moderate speed until all solids had melted at 95 Celsius degrees.
3. The temperature was slightly lowered to 85 Celsius degrees and pigments, tricaprylin and mica were added.
4. The contents of main beaker A was transferred to a Silverson mixer for emulsification while maintaining the temperature at 85-90 Celsius degrees.
5. In a separate beaker 2, glycerin and PEI-35 were added into DI water and mixed and heated to 85 Celsius degrees.
6. The contents of side beaker B was added dropwise into the beaker A while emulsifying at 9000 rpm under the Silverson mixer for 30 minutes.
7. Afterward, the emulsification speed was lowered to 2000 rpm for 5 minutes and was cooled to 25 Celsius degrees.
The contents of main beaker A was poured into container.

EXAMPLE 10

Mascara Composition

Step One: Make the PPMA-PEI Gel

| Phase | Component | Example 10 Gel |
| --- | --- | --- |
| A | Caprylic/capric Triglyceride | 1 |
| A | Polylene ethylene Maleic Anhydride Copolymer | 9.33 |
| A | Iron Oxides | 8 |
| A | Isododecane | 39.92 |
| A | Propylparaben | 0.2 |
| B | DI Water | 34 |
| B | Disodium EDTA | 0.1 |
| B | Potassium Cetyl Phosphate | 2 |
| B | Methylparaben | 0.25 |
| B | Pentylene Glycol | 2 |
| B | PEI-35 | 2 |
| C | Simethicone | 0.1 |
| D | Phenoxyethanol (and) Methylparaben (and) Isopropylparaben (and) Isobutylparaben (and) Butylparaben | 1.1 |
| | Total | 100 |

Procedures
1. In the main beaker A, add Isododecane, Caprylic/capric Triglyceride, Polylene ethylene Maleic Anhydride Copolymer, Propylparaben. Heat the content to 90° C. until all solids have melted.
2. Add Iron Oxides into main beaker and start homogenizing batch for 1 h at 850 RPM. (Temperature Maintained at 85-90° C.)
3. In a side beaker B, add ID water, Disodium EDTA, Potassium Cetyl Phosphate, Methylparaben, Pentylene Glycol. Mix until uniform. Heat content to 90° C.
4. In the side beaker B, Add PEI, Mix until PEI dissolved. (Temperature maintained at 85-90° C.)
5. Slowly add side beaker B to main beaker A. Then add Simethicone to the mixture. The gel formation was observed in 5 minutes after mixing A and B.
6. During the gel formation, slow down the mixing speed from 250 RPM to 100 RPM to 50 RPM.
7. Once the gel network became thick enough, change to sweep blade. Start cooling using 50 RPM.
8. At 35° C., add the mixture of Phenoxyethanol (and) Methylparaben (and) Isopropylparaben (and) Isobutylparaben (and) Butylparaben.
9. Continue cooling to 25° C. and drop batch at 25° C.

Step Two: Blend Polyol with PPMA-PEI Gel

| Phase | Component | Example 10 |
| --- | --- | --- |
| A | PPMA-PEI Gel | 90 |
| A | Hyperbranched Polyalpha Olefins | 10 |
| | Total | 100 |

Procedure:
1. Heated the Hyperbranched Polyalpha Olefins to 40° C.
2. Blended the PPMA-PEI gel with Hyperbranched Polyalpha Olefins according to 9:1 ratio under 200 RPM for 20 mins.

EXAMPLE 11

| | |
| --- | --- |
| isohexadecane | 2.25 |
| isododecane | 40.15 |
| PP207* | 6.75 |
| polyglyceryl-2 triisostearate | 2.50 |
| DI Water | 25.50 |
| Cellulose | 0.20 |
| Hyperbranched polyol | 10.00 |

-continued

| | | |
|---|---|---|
| Polyethyleneimine | 0.75 | |
| TITANIUM DIOXIDE | 7.82 | |
| IRON OXIDES | 1.46 | |
| IRON OXIDES | 0.52 | |
| IRON OXIDES | 0.20 | |
| DISODIUM EDTA | 0.20 | |
| propylene glycol | 0.50 | |
| PHENOXY-2 ETHANOL | 0.80 | |
| CHLORPHENESIN | 0.20 | |
| ETHYL PARABEN | 0.20 | |
| TOTAL | 100.00 | |

*PP207 is a linear polypropylene-ethylene-maleic anhydride copolymer wax commercially available from Clariant under the tradename LICOCARE PP207 LP 3349.

Procedure
1. In container A, PP207 was melted in the isohexadecane and isododecane until fully dissolved. The temperature was brought to 90° C.
2. While maintaining the temperature, the hyperbranched polyol, emulsifier and pigment grind were added to container A until fully dissolved.
3. In separate container B, water, Polyethyleneimine, cellulose, and preservatives were mixed at 90 C
4. B was added to A slowly at high sheer (~700 rpm).
5. Heat was maintained at 70° C.-80° C. for 20 minutes while maintaining high sheer mixing.
6. The mixture was cooled to room temperature while mixing.

EXAMPLE 12

Lipstick

| Phase | Chemical Name | % wt/wt |
|---|---|---|
| A | Octododecanol | 10.50% |
| A | Octyldodecyl Neopantanoate | 10.00% |
| A | HYDROGENATED POLYISOBUTENE | 20.35% |
| A | POLYBUTENE | 5.00% |
| A | Isohexadecane | 3.00% |
| A | Tricaprylin | 6.58% |
| B | C26-C28 Polar Modified Wax | 7.00% |
| B | Polyethylene 400 | 4.00% |
| B | Polyethylene 500 | 4.00% |
| B | Ozokerite | 0.50% |
| B | VP/Eicosene Copolymer | 3.00% |
| B | Color Pigments and Pearls | 7.07% |
| C | Deionized Water | 15.00% |
| C | PEI-35 | 0.25% |
| C | Preservatives | 0.75% |
| C | Glycerin | 3.00% |

Procedure
1. Phase A materials were added to a suitable size beaker A and heated to 95 Celsius degrees.
2. When mixture was uniform phase B materials were added and heated to 95 Celsius degrees.
3. When enough solids had melted, the contents were mixed with moderate speed until all solids had melted at 95 Celsius degrees.
4. The temperature was slightly lowered to 85 Celsius degrees.
5. The contents of main beaker A were transferred to a Silverson mixer for emulsification while maintaining the temperature at 85-90 Celsius degrees.
6. In a separate beaker 2, phase C materials were added and mixed and heated to 85 Celsius degrees.
7. The contents of side beaker B were added dropwise into the beaker A while emulsifying at 9000 rpm under the Silverson mixer for 30 minutes. Afterward, the emulsification speed was lowered to 2000 rpm for 5 minutes.
8. The contents were poured into lipstick molds at 80 Celsius degrees.
9. The lipstick in molds was placed in a cooling tunnel for minutes at −10 Celsius degrees. Once cooled, the lipstick in molds were removed from the cooling tunnel to equilibrate to 25 Celsius degrees and removed from the molds after lipsticks had thawed to 25 Celsius degrees.

EXAMPLE 13

Mascara Composition

| Phase | Chemical Name | % wt/wt |
|---|---|---|
| A | Propylparaben | 0.20 |
| A | Isododecane | 28.00 |
| A | Oil-soluble polar modified polymer | 13.33 |
| A | Iron Oxides | 8.00 |
| A | Hyperbranched Polyol | 20.00 |
| B | DI Water | 26.92 |
| B | Disodium EDTA | 0.10 |
| B | Potassium Cetyl Phosphate | 2.00 |
| B | Methylparaben | 0.25 |
| C | Simethicone | 0.10 |
| D | PHENOXYETHANOL (and) METHYLPARABEN (and) ISOPROPYLPARABEN (and) ISOBUTYLPARABEN (and) BUTYLPARABEN | 1.10 |

Procedure
In a suitable size metal container A, propylparaben, Oil-soluble polar modified polymer and Hyperbranched Polyol were added and heat to 90 C or until all solids had
1. melted.
2. When all solids had melted, Isododecane was added to batch.
3. Iron oxides was added to batch and was homogenized for at least 1 hour.
In side tank B with water bath, phase B was added and mixed into batch until
4. uniform. Batch was heated to 90 C.
5. Mix side tank B for 20 minutes.
When both tanks were at temperature, side tank B was slowly added to main tank A
6. while homogenizing at 850 rpm.
After 5 minutes of homogenizing, Simethicone was added to batch and
7. homogenized for 30 minutes at 90 C.
8. Batch was cooled naturally to 25 C.
9. Phase D was added to container A at 35 C and was furthered cooled to 25 C.
10. The contents were poured into appropriate containers.

EXAMPLE 14

Lipstick

| Phase | Chemical Name | Ex 14 |
|---|---|---|
| A | Polyglyceryl-2 Triisostearate | 3.00 |
| A | Octyldodecyl Neopantanoate | 14.18 |

| Phase | Chemical Name | Ex 14 |
|---|---|---|
| A | Hydrogenated Polydecene | Q.S. |
| A | Hyperbranched polyol | 5.00 |
| A | Polyethylene 400 | 8.00 |
| A | Oil-soluble polar modified polymer | 7.00 |
| A | Tricaprylin | 13.80 |
| A | Color pigments | 5.00 |
| A | Mica | 2.00 |
| B | Deionized Water | 22.50 |
| B | Glycerin | 3.00 |

Procedure
1. The following were added to a suitable size beaker A and heated to 95 Celsius degrees: Polyglyceryl-2 Triisosterate, octyldodecyl neopantanoate, hydrogenated polydecene, Hyperbranched poloyl, polyethylene 400, Color pigment, Oil-soluble polar modified polymer, tricaprylin.
2. When enough solids had melted, the contents were mixed with moderate speed until all solids had melted at 95 Celsius degrees.
3. The temperature was slightly lowered to 85 Celsius degrees and pigments and mica were added.
4. The contents of main beaker A was transferred to a Silverson mixer for emulsification while maintaining the temperature at 85-90 Celsius degrees.
5. In a separate beaker 2, glycerin was added into DI water and mixed and heated to 85 Celsius degrees.
6. The contents of side beaker B was added dropwise into the beaker A while emulsifying at 9000 rpm under the Silverson mixer for 30 minutes.
7. Afterward, the emulsification speed was lowered to 2000 rpm for 5 minutes.
8. The contents were poured into lipstick molds at 80 Celsius degrees.
9. The lipstick in molds was placed in a cooling tunnel for minutes at −10 Celsius degrees. Once cooled, the lipstick in molds were removed from the cooling tunnel to equilibrate to 25 Celsius degrees and removed from mold after lipsticks had thawed to 25 Celsius degrees.

EXAMPLE 15

Lip Gloss

| Phase | Chemical Name | Ex 15 |
|---|---|---|
| A | Polyglyceryl-2 Triisosterate | 6.00 |
| A | Octyldodecyl Neopantanoate | 5.93 |
| A | Hydrogenated Polydecene | Q.S. |
| A | Hyperbranched polyol | 5.00 |
| A | Oil-soluble polar modified polymer | 10.00 |
| A | Tricaprylin | 13.80 |
| A | Color pigments | 5.00 |
| A | Mica | 2.00 |
| B | Deionized Water | 40.00 |
| B | Glycerin | 3.00 |

Procedure
1. The following were added to a suitable size beaker A and heated to 95 Celsius degrees: Polyglyceryl-2 Triisosterate, octyldodecyl neopantanoate, hydrogenated polydecene, Hyperbranched polyol, Color pigment, Oil-soluble polar modified polymer, tricaprylin.
2. When enough solids had melted, the contents were mixed with moderate speed until all solids had melted at 95 Celsius degrees.
3. The temperature was slightly lowered to 85 Celsius degrees and pigments and mica were added.
4. The contents of main beaker A was transferred to a Silverson mixer for emulsification while maintaining the temperature at 85-90 Celsius degrees.
5. In a separate beaker 2, glycerin was added into DI water and mixed and heated to 85 Celsius degrees.
6. The contents of side beaker B was added dropwise into the beaker A while emulsifying at 9000 rpm under the Silverson mixer for 30 minutes.
7. Afterward, the emulsification speed was lowered to 2000 rpm for 5 minutes.
8. The contents of main beaker A was poured into container.

EXAMPLE 16

Foundation

| | Chemical Name | Weight % |
|---|---|---|
| A | isododecane | Q.S. |
| | Oil-soluble polar modified polymer | 6 |
| | hyperbranched polyol | 10 |
| | Pigments | 10 |
| | polyglyceryl-2-triisostearate | 2.5 |
| B | DI Water | 25.5 |
| | cellulose | 0.2 |
| | PHENOXY-2 ETHANOL | 0.80 |
| | Total | 100 |

Procedure
1. In container A, Oil-soluble polar modified polymer and Hyperbranched Polyol were melted in isododecane until fully dissolved. The temperature was brought to 900 C.
2. While maintaining the temperature, polyglyceryl-2-triisostearate and pigment were added to container A until fully dissolved.
3. In a separate container B, water, glycerin, and preservatives were mixed and heated to 90° C.
4. The contents of container B were added to the contents of container A slowly at high sheer (1000 rpm).
5. Heat was maintained at 70° C.-80° C. for 20 minutes while maintaining high sheer mixing.
6. The mixture was cooled to room temperature while mixing.

EXAMPLE 17 and 18

Emulsions

| Phase | INCI Name | EX 17 WT % | EX 18 WT % |
|---|---|---|---|
| A1 | Octyldodecyl Neopantanoate | 33.33 | 33.33 |
| A2 | Hydrogenated Polydecene | 33.33 | 33.33 |
| A3 | Hyperbranched polyol Polypropylene-ethylene-maleic acid anhydride copolymer wax in Isohexadecane (75% solid) | 0.00 | 10.00 |
| A4 | (Licocare PP207) | 13.33 | 13.33 |
| B1 | Deionized Water | 10.00 | 10.00 |
| 2 | Glycerin (polyol) | 10.00 | 0.00 |
| | Total | 100.00 | 100.00 |

Procedure
1. In a container A, oils were added and heated to 90 Celsius degrees. Then the Licocare PP207 was added and mixed until the wax was melted. The polyol was added later and mixed.
2. In another container, phase B was prepared and heated to 80 Celsius degrees.
3. Phase B was slowly added to phase A and mixed at a speed of 2000 rpm for 30 minutes.
4. The mixture was slowly cooled to room temperature while the mixing speed was kept at 2000 rpm.
5. The resulting materials were gels.

EXAMPLEs 19-22

Anhydrous Compositions

| Phase | INCI Name | EX 19 Wt % | EX 20 Wt % | EX 21 Wt % | EX 22 Wt % |
|---|---|---|---|---|---|
| A1 | Hydrogenated Polydecene | 38.33 | 76.67 | 0.00 | 0.00 |
| A2 | Octyldodecyl Neopantanoate | 38.33 | 0.00 | 0.00 | 0.00 |
| A3 | Isohexadecane | 0.00 | 0.00 | 76.67 | 0.00 |
| A4 | Isododecane | 0.00 | 0.00 | 0.00 | 76.67 |
| A5 | Hyperbranched polyol | 10.00 | 10.00 | 10.00 | 10.00 |
| A6 | Polypropylene-ethylene-maleic acid anhydride copolymer wax in Isohexadecane (75% SOLID) (Licocare PP 207) | 13.33 | 13.33 | 13.33 | 13.33 |
| | Total | 100.00 | 100.0 | 100.0 | 100.0 |

Procedure
1. In a container A, oils were added and heated to 90 Celsius degrees. Then the Licocare PP207 was added and mixed until the wax was melted. The hyperbranched polyol was added later and mixed.
2. Mixing was conducted for 20 hours and the resulting products were in the gel state.

EXAMPLE 23

Anhydrous Composition

| Phase | INCI Name | EX 23 WT % |
|---|---|---|
| A1 | Hydrogenated Polydecene | 75.37 |
| A2 | Hyperbranched polyol | 10.00 |
| A3 | Polypropylene-ethylene-maleic acid anhydride copolymer wax in Isohexadecane (75% SOLID) (Licocare PP 207) | 13.33 |
| B | Aqueous Citric acid | 1.30 |
| | Total | 100.00 |

Procedure
1. In a container A, oils were added and heated to 90 Celsius degrees. Then the Licocare PP207 was added and mixed until the wax was melted. The hyperbranched polyol was added later and mixed.
2. The aqueous citric acid was added slowly to the mixture in container A.
3. The mixture was heated at 90 Celsius degrees and kept for 24 hours.
4. The mixture was slowly cooled to room temperature while the mixing speed was kept at 2000 rpm.
5. The resulting material is a gel.

EXAMPLE 24

Lipstick

| INCI Name | |
|---|---|
| Hydrogenated Polyisobutene | 3.0 |
| Octyldodecyl Neopentanoate | 4.8 |
| VP/hexadecene copolymer | 6.6 |
| Regalite | 8 |
| Reaction product from example 8 | 10 |
| isododecane | 16.79 |
| BIS-BEHENYL/ISOSTEARYL/PHYTOSTERYL DIMER DILINOLEYL DIMER DILINOLEATE | 5.15 |
| isohexadecane | 21.57 |
| BLUE 1 LAKE | 0.12 |
| RED 7 | 0.77 |
| TITANIUM DIOXIDE | 1.58 |
| IRON OXIDES | 1.13 |
| IRON OXIDES | 0.34 |
| IRON OXIDES | 0.32 |
| VP/EICOSANE COPOLYMER | 1 |
| POLYGLYCEROL 3 BEESWAX | 1.7 |
| POLYETHYLENE 400 | 5.5 |
| POLYETHYLENE 500 | 6.6 |
| PEARL | 0.38 |
| PEARL | 3.35 |
| Mica | 1.3 |
| HDI/TRIMETHYLOL HEXYLLACTONE | 1 |
| Total | 100.0 |

EXAMPLE 25

| | |
|---|---|
| Isohexadecane | 2.25 |
| Isododecane | 40.90 |
| PP207* | 6.75 |
| polyglyceryl-2 triisostearate | 2.50 |
| DI Water | 25.50 |
| Cellulose | 0.20 |
| Hyperbranched Polyol | 10.00 |
| TITANIUM DIOXIDE | 7.82 |
| IRON OXIDES | 1.46 |
| IRON OXIDES | 0.52 |
| IRON OXIDES | 0.20 |
| DISODIUM EDTA | 0.20 |
| propylene glycol | 0.50 |
| PHENOXY-2 ETHANOL | 0.80 |
| CHLORPHENESIN | 0.20 |
| ETHYL PARABEN | 0.20 |
| TOTAL | 100.00 |

*PP207 is a linear polypropylene-ethylene-maleic anhydride copolymer wax commercially available from Clariant under the tradename LICOCARE PP207 LP 3349.

Procedure
1. In container A, PP207 was melted in the isohexadecane and isododecane until fully dissolved. The temperature was brought to 90° C.
2. While maintaining the temperature, the hyperbranched polyol, emulsifier and pigment grind were added to container A until fully dissolved.

3. In separate container B, water, cellulose, and preservatives were mixed at room temperature.
4. B was added to A slowly at high sheer (~700 rpm).
5. Heat was maintained at 70° C.-80° C. for 20 minutes while maintaining high sheer mixing.
6. The mixture was cooled to room temperature while mixing.

EXAMPLE 26

Lipstick

| Phase | Chemical Name | Example 1 |
| --- | --- | --- |
| A | Non-volatile Solvent | Q.S. |
| A | Hyperbranched polyol | 5.00 |
| A | Polyethylene 400 | 8.00 |
| A | C26-28 polar modified wax | 7.00 |
| A | Pigment | 3.50 |
| A | Mica | 2.00 |
| B | Deionized Water | 22.50 |
| B | Glycerin | 3.00 |
| | Total | 100.00 |

Procedure:
1. The following were added to a suitable size beaker A and heated to 95 Celsius degrees: non-volatile solvent, hyperbranched polyol, polyethylene 400, $C_{26-28}$ polar modified wax.
2. When enough solids had melted, the contents were mixed with moderate speed until all solids had melted at 95 Celsius degrees.
3. The temperature was slightly lowered to 85 Celsius degrees and pigments and mica were added.
4. The contents of main beaker A was transferred to a Silverson mixer for emulsification while maintaining the temperature at 85-90 Celsius degrees.
5. In a separate beaker 2, glycerin was added into DI water and mixed and heated to 85 Celsius degrees.
6. The contents of side beaker B was added dropwise into the beaker A while emulsifying at 9000 rpm under the Silverson mixer for 30 minutes. Afterward, the emulsification speed was lowered to 2000 rpm for 5 minutes.
7. The contents were poured into lipstick molds at 80 Celsius degrees.
8. The lipstick in molds was placed in a cooling tunnel for 15 minutes at −10 Celsius degrees. Once cooled, the lipstick in molds were removed from the cooling tunnel to equilibrate to 25 Celsius degrees and removed from mold after lipsticks had thawed to 25 Celsius degrees.

EXAMPLE 27

Lip Gloss

| Phase | Chemical Name | Example 27 |
| --- | --- | --- |
| A | Non-volatile Solvent | Q.S. |
| A | $C_{26-28}$ polar modified wax | 7.00 |
| A | Hyperbranched polyol | 5.00 |
| A | Pigment | 3.50 |
| A | Mica | 2.00 |
| B | Deionized Water | 40.00 |
| B | Glycerin | 3.00 |
| | Total | 100.00 |

Procedure:
1. The following were added to a suitable size beaker A and heated to 95 Celsius degrees: non-volatile solvent, hyperbranched polyol, $C_{26-28}$ polar modified wax.
2. When enough solids had melted, the contents were mixed with moderate speed until all solids had melted at 95 Celsius degrees.
3. The temperature was slightly lowered to 85 Celsius degrees and pigments and mica were added.
4. The contents of main beaker A was transferred to a Silverson mixer for emulsification while maintaining the temperature at 85-90 Celsius degrees.
5. In a separate beaker 2, glycerin was added into DI water and mixed and heated to 85 Celsius degrees.
6. The contents of side beaker B was added dropwise into the beaker A while emulsifying at 9000 rpm under the Silverson mixer for 30 minutes. Afterward, the emulsification speed was lowered to 2000 rpm for 5 minutes until contents were cooled to 25 Celsius degrees.
7. The contents of main beaker A was poured into container.

EXAMPLE 28

Foundation

| | Chemical Name | % |
| --- | --- | --- |
| A | isododecane | Q.S. |
| | C26-28 polar modified wax | 10 |
| | hyperbranched polyol | 10 |
| | Pigment | 10 |
| | polyglyceryl-2-triisostearate | 2.5 |
| B | DI Water | 25.5 |
| | cellulose | 0.2 |
| | PHENOXY-2 ETHANOL | 0.80 |
| | Total | 100 |

Procedure
1. In container A, Oil-soluble high carbon polar modified polymer and hyperbranched polyol was melted in isododecane until fully dissolved. The temperature was brought to 900 C.
2. While maintaining the temperature, polyglyceryl-2-triisostearate and pigment were added to container A until fully dissolved.
3. In a separate container B, water, cellulose, and preservatives were mixed and heated to 90° C.
4. The contents of container B were added to the contents of container A slowly at high sheer (1000 rpm).
5. Heat was maintained at 70° C.-80° C. for 20 minutes while maintaining high sheer mixing.
6. The mixture was cooled to room temperature while mixing.

EXAMPLEs 29-34

Reaction Product

| Chemical Name | Trade Name | EX 29 | EX 30 | EX 31 | EX 32 | EX 33 | EX 34 |
|---|---|---|---|---|---|---|---|
| Isohexadeane | | 78.00 | 78.00 | 70.00 | 64.00 | 64.00 | 50.00 |
| Hyperbranched polyol | | 7.00 | 11.00 | 10.00 | 18.00 | 11.00 | 25.00 |
| C26-C28 ALPHA OLEFIN MALEIC ACID ANHYDRIDE COPOLYMER | Licocare CM 401 LP3345 | 15.00 | 11.00 | 20.00 | 18.00 | 25.00 | 25.00 |
| | | 100.00 | 100.00 | 100.00 | 100.00 | 100.00 | 100.00 |

Procedure
1. In a container A, oil was added and heated to 110 Celsius degrees. Then the Licocare CM401 was added and mixed until the wax was melted.
2. Then, the hyperbranched polyol was added and mixed at 140 Celsius degrees.
3. Mixing was conducted from 45 minutes to 6 hours until the resulting products were in the gel state.

What is claimed is:

1. A composition comprising: a reaction product of (a) a hyperbranched polyol; and (b) at least one polar modified polymer.

2. The composition of claim 1, further comprising at least one volatile.

3. The composition of claim 1, further comprising at least one non-volatile oil.

4. The composition of claim 1, wherein the polar modified polymer is present in an amount of from about 1% to about 30% by weight, based on the weight of the composition.

5. The composition of claim 1, wherein the polar modified polymer is a polypropylene and/or polyethylene-maleic anhydride modified wax.

6. The composition of claim 1, wherein the polar modified polymer is an oil-soluble polar modified polymer.

7. The composition of claim 1, wherein the polar modified polymer is an oil-soluble high carbon polar modified polymer.

8. The composition of claim 1, further comprising water in an amount of from about 5 to about 50% by weight, based on the weight of the composition.

9. The composition of claim 1, in the form of an emulsion.

10. The composition of claim 1, wherein the hyperbranched polyol has a hydroxyl number between 100 and 200.

11. The composition of claim 1, wherein the hyperbranched polyol is present in an amount of from about 0.1 to about 15% by weight, based on the weight of the composition.

12. A method of making-up a keratinous substrate comprising applying onto the substrate in an amount sufficient to make up the substrate the composition of claim 1.

13. The composition of claim 1, wherein the reaction product is obtained by reacting at least two hydroxyl groups of the hyperbranched polyol to hydrophilic groups on the polar modified polymer.

* * * * *